United States Patent
Kondo et al.

[11] Patent Number: 5,089,230
[45] Date of Patent: Feb. 18, 1992

[54] REAGENT REACTOR APPARATUS

[75] Inventors: Akihiro Kondo, Mukoh; Yoshiyuki Kato, Kyoto; Ikunoshin Kato, Uji; Hisao Tsuruta, Takatsuki, all of Japan

[73] Assignees: Takara Shuzo Co.; Irica Instruments, Inc., both of Kyoto, Japan

[21] Appl. No.: 491,565

[22] Filed: Mar. 9, 1990

[30] Foreign Application Priority Data

Mar. 15, 1989 [JP] Japan .................................. 1-64377

[51] Int. Cl.⁵ ............................................ G01N 35/00
[52] U.S. Cl. ........................................ 422/64; 422/63; 422/72; 436/43; 436/45; 73/864.24
[58] Field of Search ................ 73/864.24; 422/63, 64, 422/72; 436/43, 45

[56] References Cited

U.S. PATENT DOCUMENTS 3,487,862  1/1970  Soderblom ........................... 141/130
3,826,622  7/1974  Natelson ............................... 422/102
4,197,735  4/1980  Munzer et al. ..................... 73/864.24

Primary Examiner—Robert J. Warden
Assistant Examiner—Stephanie Blythe
Attorney, Agent, or Firm—Morgan & Finnegan

[57] ABSTRACT

A reagent reaction apparatus for automatically performing a reaction by introducing various kinds of reagents to a sample solution. The reagent reaction apparatus includes a number of sample vials within a containing section and a plunger valve with fluid introducing port and a fluid discharge port located on top of the containing section. A mechanism sequentially injects into the sample vial a predetermined amount of reagents into a sample vial containing a measured amount of sample solutions. The sample vial is held in a rotary cone in order to apply centrifugal force. Then, the sample solution and reagents are subjected top a temperature adjusting bath which is preselected for the required reaction temperature. A mechanism transports the final product in the sample vial to a discharge station.

5 Claims, 10 Drawing Sheets

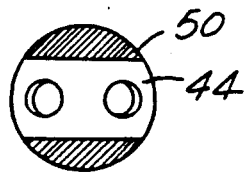
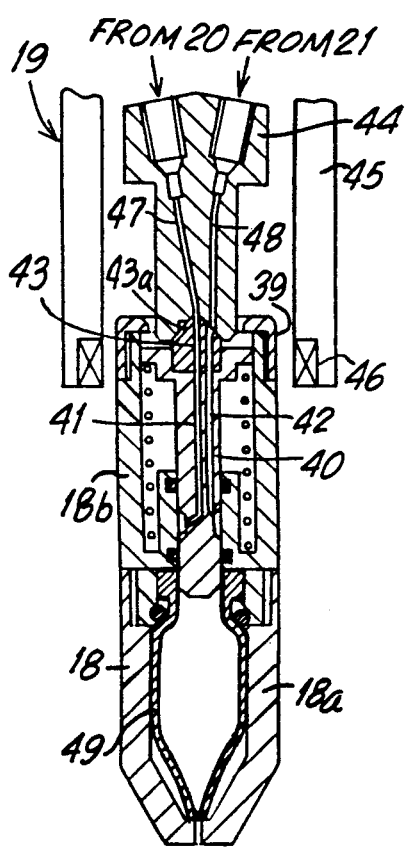
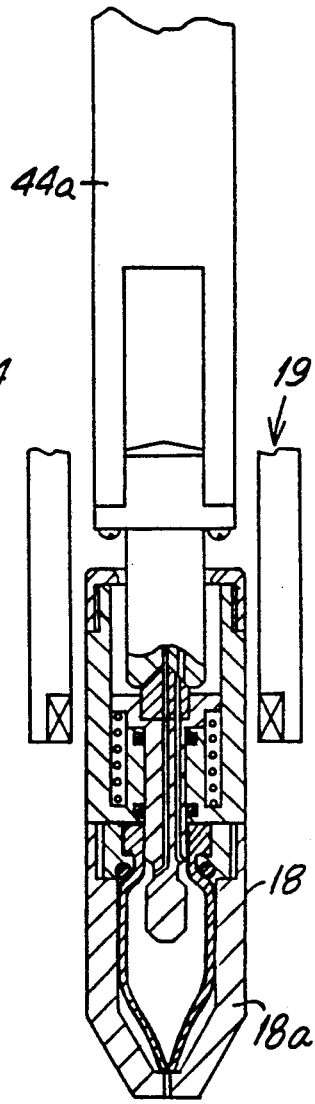
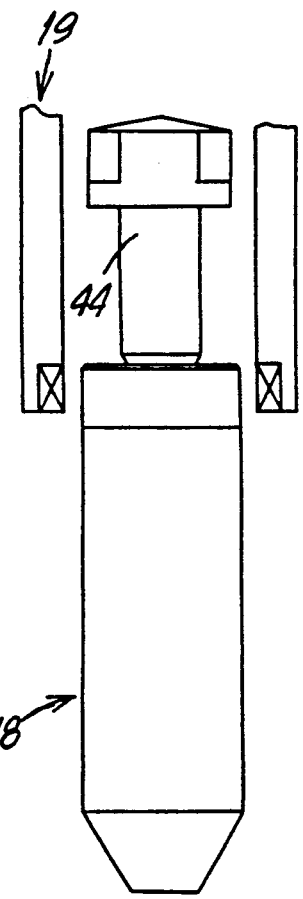
FIG.6D
FIG.6A   FIG.6B   FIG.6C

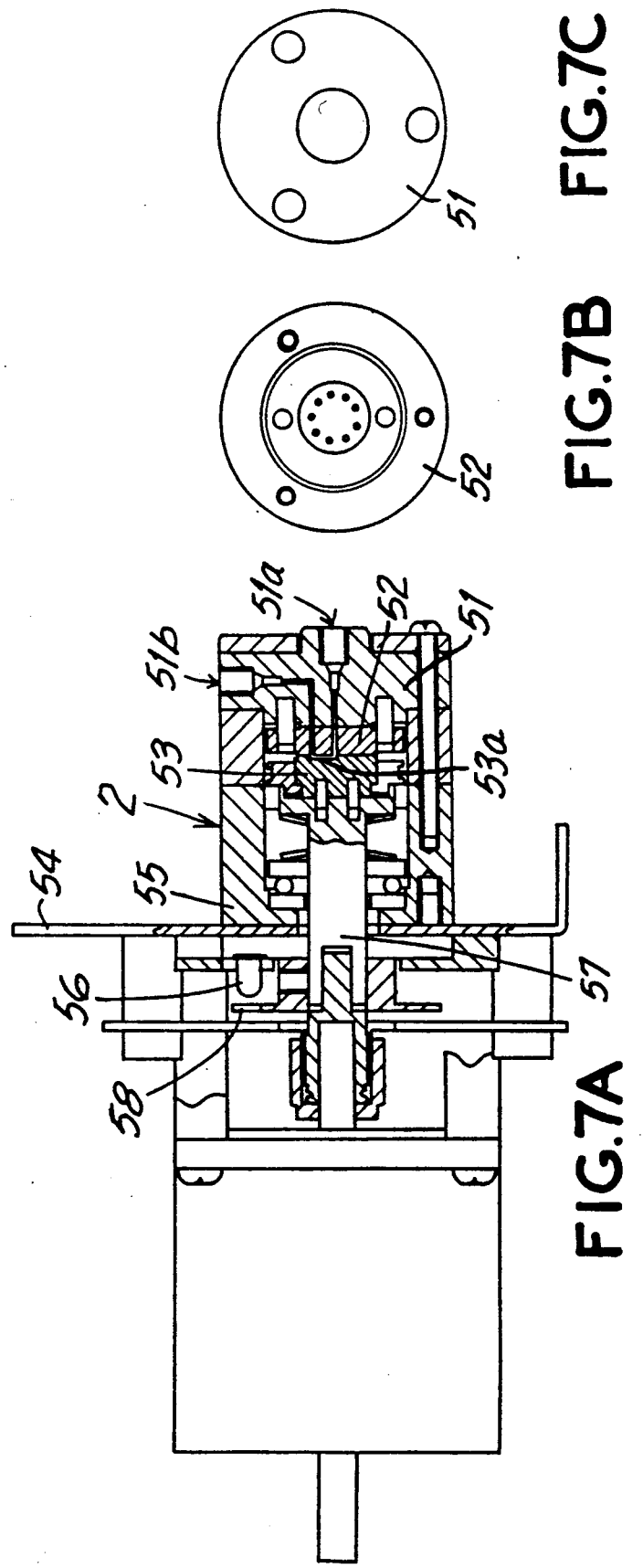

2

REAGENT REACTOR APPARATUS

FIELD OF THE INVENTION

The present invention relates to a reagent reactor apparatus for introducing various kinds of reagents into a sample solution so as to react them with each other.

PRIOR ART

Heretofore, in processing a liquid sample in which reagent reactions are required to be sequentially carried out, for example, a process for attaching a fluorescent label to a saccharide which has been isolated from a glycoconjugate so as to analyze the glycoconjugate is manually carried out as done in a laboratory because it is necessary to handle many kinds of reagents depending on the number of reactions.

However, it is very troublesome to appropriately add reagents to a sample without contaminating the sample and manually manage reaction conditions and known apparatuses are incapable of making a fine adjustment in performing these operations.

It is the object of the invention to provide a reagent reactor apparatus capable of automatically performing a process for performing a reaction by introducing various kinds of reagents to a sample solution.

DISCLOSURE OF THE INVENTION

In accomplishing the above object, according to the invention, a reagent reaction apparatus comprises:

a plurality of sample vials having on the top of the containing section thereof a plunger valve having a fluid introducing port and a fluid discharge port;

first vial transporting means for sequentially transporting the plurality of sample vials to a start position along a predetermined path;

second vial transporting means for receiving the sample vials at a collecting position set a predetermined distance apart from the start position and sequentially feeding out the sample vials along a second predetermined path;

at least one temperature adjusting bath arranged in a range between the start position and collecting positions;

means, disposed at a position in the range, for converging liquid located in an upper portion of the sample vial which the means has received to the bottom thereof by applying physical force from the opening of the sample vial toward the bottom thereof; and sample vial operating means for transporting the sample vial from the start position to the collecting position at which the sample vial is released, by lifting the sample vial from the start position to a predetermined transporting level, through the range to a position just above the collecting position, and lowering it from the position to the collecting position, the passing of the sample vial by the operating means through the range, in the order according to a predetermined sequence program, including midway steps of forwardly or backwardly moving the sample vial to a position above either the at least one temperature adjusting bath or the converging means, lowering the sample vial thereinto where the operating means releases or grasps the sample vial to put it in or take out it from either the bath or the converging means, and lifting it up to the transporting level; and the vial operating means being provided with a fluid supply passage and a fluid discharge passage for selectively conveying any one of a plurality of reagents or an inert gas, wherein when the vial operating means holds one of the sample vials, the protruding ends of the passages respectively communicate with the fluid introducing port and the fluid discharge port formed in the plunger valve disposed in the sample vial; and the fluid introducing port and the fluid discharge port are opened by pressing the plunger valve downward with respect to the main body of the sample vial.

In the above construction, in order to converging, or dropping liquid located in an upper portion of the sample vial to the bottom thereof by applying a physical force from the opening of the sample vial to the bottom thereof, a means for applying a centrifugal force to the liquid or a means of applying vibration to the sample vial may be adopted. These liquid dropping means allow a reaction solution to be agitated as well. The reactant solution may be stirred by an agitating member inserted thereinto, an ultrasonic process, an electron beam or the like.

The discharge in accordance with the invention means the removal of a reagent and a washing liquid from the sample vial and the passage for the reagent. In order to discharge the reagent, the discharge passage is connected to the discharge port so as to remove the reagent or the washing liquid through the discharge passage by means of a sucking, or a pressure application from the other passage. A suction pump or a vacuum source may be employed as a suction means. An inert gas may be used as a pressure applying means.

The introduction of a reagent into the sample vial and the transportation of the sample vial can be preferably carried out by the following combination of the sample vial and the operating mechanism of the reagent reactor apparatus in accordance with the invention. That is, the sample vial comprises:

a containing section;

a valve sleeve fixedly connected to the top of the opening of the containing section, at least a part of which consists of a magnetic material;

a plunger valve held in the valve sleeve so as to penetrate into and retracted from the containing section and having a fluid introducing port and a fluid discharge port each provided with an outside-connecting opening formed on the top surface thereof and a containing section-communicating opening formed on the lower section thereof; each of the containing section-communicating openings being exposed to the containing section when the plunger valve has penetrated into the containing section and the bottom, or end portion of the plunger valve engages the entrance of the containing section when the plunger valve has retracted; and a retaining spring for retaining the plunger valve in the uppermost position thereof so as to seal the containing section by normally forcing the each containing section-communicating opening to be positioned outside the containing section.

The sample vial operating means comprises:

a downward sleeve provided with a solenoid for selectively exerting a magnetic attraction to a magnetic material mounted on the valve sleeve of the sample vial;

a nose main body held in the downward sleeve at a predetermined position thereof; the lower end thereof contacting with the conic projecting surface of the plunger valve of the sample vial or the plunger valve in such an extent as to press the plunger valve downward slightly when the downward sleeve located directly above the sample vial is in a level from which the solenoid is capable of applying a magnetic force to the magnetic material; the nose main body being provided with a fluid supply passage and a fluid discharge passage each communicating with the respective outside-connecting openings of the fluid introducing port and the fluid discharge port formed in the plunger valve when the lower end thereof contacts the plunger valve or the conic projecting surface thereof; and a movable nose provided with a movable holding member for holding the downward sleeve which holds the nose main body at the predetermined position thereof, the movable holding member allowing the downward sleeve and the nose main body to vertically move between the lowermost position in which the downward sleeve and the nose main body press the plunger valve of the sample vial downward to the position at which each of the containing section-communicating openings is exposed to the containing section when the lower end surface of the nose main body contacts with the upper end surface of the plunger valve and the uppermost position in which the downward sleeve and the nose main body lift the sample vial by at least the whole length thereof with the solenoid magnetically attracting the magnetic material thereto. In this construction, the movable nose is capable of accomplishing the operation in the uppermost position within a predetermined range in which many sample vials are horizontally arranged to be processed.

According to this construction, the fluid supply passage of the nose is selectively connected to a reagent supply source or an inert gas source and the fluid discharge passage of the nose is connected to a fluid sucking means so as to perform a process for sequentially injecting reagents into the sample vial and allowing reactions of the reagents according to a sequence program.

A centrifugal force applier is employed as a means for dropping a reagent toward the bottom of the sample vial of the reagent apparatus in accordance with the invention.

The centrifugal force applier comprises a rotary cone having at least a pair of holes for receiving a plurality of sample vials arranged thereon circularly or symmetrical with respect to the center of the rotary cone. The axes of the respective holes coinciding with the base line of an imaginary conic surface which makes less than 45° with the axis of the rotary cone and the axis of the rotary cone making more than 45° with the horizontal line. According to this construction, centrifugal force is applied to liquid contained in the sample vial when the sample vial is rotated after the sample vial is received by the hole which has rotated to the lowermost position of the rotational orbit of the rotary cone where the sample vial already received, if any, is to be ready for taking out and the opening of the sample vial held by the hole which has rotated to the highest point of the rotational orbit of the rotary cone is held at a position higher than the bottom thereof.

According to the entire construction of the reagent reactor apparatus in accordance with the invention, after the sample vial containing an appropriate amount of a sample solution is placed on the first transporting means, predetermined reagents are sequentially injected into the sample vial according to the sequence program, then, the reagents are mixed with each other and react with each other, and washed. These processes are automatically carried out for each vial not for a group of vials. Therefore, the reagents can be processed in substantially the same condition and as such, a reagent reactor apparatus preferable in reproducibility can be provided. Further, since the heat capacity of each sample vial is small, the sample vial can always be set to a required reaction temperature or capable of reaching a predetermined temperature in a short period of time even if a temperature adjusting bath which is controlled only in a narrow temperature range is used. Thus, the reagent reactor apparatus is capable of processing reagent in a short period of time.

In the construction comprising the sample vial and the operating mechanism, only one nose member enables a preferable transportation of the sample vial, and the plunger valve accomplishes processes including the injection of the reagent into the sample vial and the fluid discharge, and the connection of passages for fluid. The plunger valve which is operated by the nose presses the plunger valve downward or releases it so as to automatically open or close the container section of the sample vial.

In addition, the centrifugal force applier applies outward and downward centrifugal force to the reagent located in the upper portion of the sample vial injected thereinto, thus dropping the reagent to the bottom of the sample vial. Thus, centrifugal force applier is effective for a reaction which is preferable in reproducibility and accuracy.

BRIEF DESCRIPTION OF THE DRAWINGS

FIGS. 6A and 6B are partial vertical sectional view showing a sample vial and a nose engaged with each other, respectively;

FIG. 6C is a front view partly in section of the sample vial and the nose engaged with each other;

FIG. 6D is a transverse sectional view showing the principal section of the nose;

FIG. 7A is a vertical sectional view of a disk valve;

FIGS. 7B and 7C are sectional views showing the construction of disks composing the passage of the disk valve;

EMBODIMENTS

Figure 1:
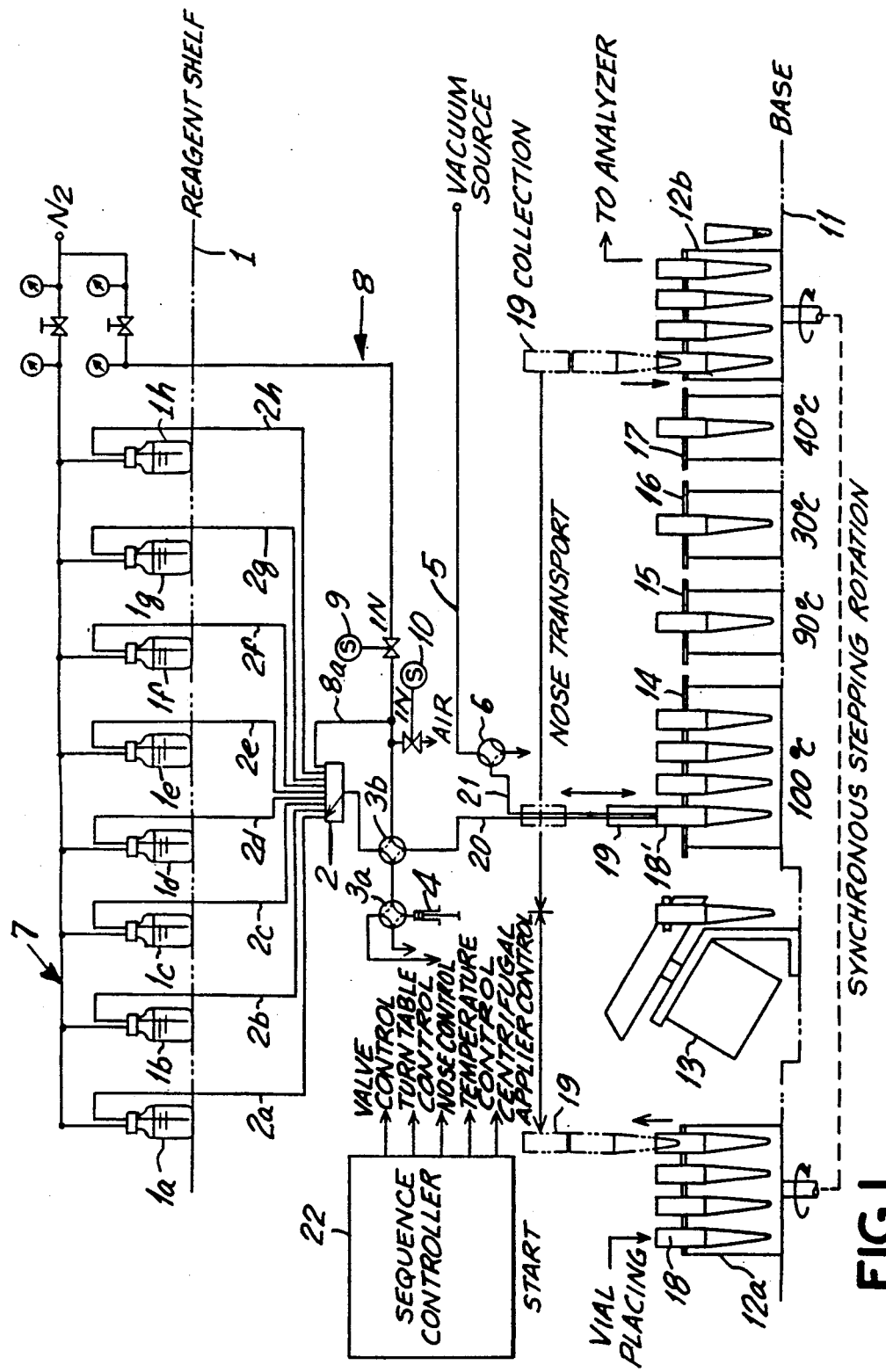
FIG. 1 is a flow diagram showing the physical arrangement of members composing a reagent reactor apparatus according to a preferred embodiment of the invention.

FIG. 1 shows the entire construction of a reagent reactor apparatus according to a preferred embodiment of the invention. Reference numerals 1a through 1h denote reagent containing bottles arranged on a reagent placing shelf 1 disposed in the upper portion of the casing (not shown) of the reagent reactor apparatus. Disposed below the reagent placing shelf 1 are a reagent selecting valve 2 consisting of a nine-way valve, a set of measuring valve 3a and 3b consisting of a four-way valve, respectively, a micro-syringe-shaped measuring device 4 connected to the measuring valve 3a, and a vacuum valve 6 shown as a four-way valve connected to a vacuum line 5. The inlet ends of the reagent selecting lines 2a through 2h of the reagent selecting valve 2 are respectively inserted into the reagent containing bottles 1a through 1h connected with branches of a first inert gas ($N_2$ in this embodiment) supply line 7 for generating pressure for feeding reagents contained in reagent containing bottles to the reagent selecting valve 2 through the reagent selecting line 2a through 2h. A second inert gas supply line 8 branched from an inert gas supply source is connected to one of the selecting ports of the reagent selecting valve 2 and the measuring valve 3b through an electromagnetic valve 9. An electromagnetic valve 10 is branched between the point from which a branch path 8a, of the inert gas supply line 8 connected to the reagent selecting valve 2, is branched and the measuring valve 3b. The second inert gas supply line 8 is selectively communicated with air. A turn table 12a disposed at the start side and a turn table 12b disposed at the collecting side are mounted on the base 11 of the reagent reactor apparatus on the left side and right side thereof, respectively. There are provided between the two tables 12a and 12b, a centrifugal force applier 13, a first temperature adjusting bath 14, a second temperature adjusting bath 15, a third temperature adjusting bath 16, a fourth temperature bath 17 in a straight line. The centrifugal force applier 13 and the temperature adjusting baths 14 through 17 receive and support a sample vial 18 (hereinafter shortly referred to as vial 18) in the same level as the turn tables 12a and 12b. A nose section 19 serving as a vial operating means is horizontally movable between the start position of the turn table 12a and the collecting position of the turn table 12b (the start position and the collecting position are set to be disposed on the inner side of the reagent reactor apparatus) and vertically movable at the start and collecting positions, and respective processing positions arranged therebetween.

The nose section 19 contacts, for example, a vial 18' disposed at the left end of the first temperature adjusting bath 14 as shown by a solid line in FIG. 1, then, presses the vial 18' downward, thus supplying a reagent or an inert gas into the vial 18' and sucking a gas therefrom. Further, the nose section 19 magnetically attracts the vial 18' thereto, thus lifting the vial 18' (at this time, the vial is sealed.) Thereafter, the nose section 19 horizontally moves between the turn tables 12a and 12b so as to transport the vial 18' to necessary processing positions. In order for the nose section 19 to perform the above operations, a measuring line 20 extending from the measuring valve 3b and a vacuum line 21 extending from the vacuum valve 6 are inserted into the nose section 19.

The operations of the respective sections of the reagent reactor apparatus described above are controlled by a sequence controller 22. It is preferable to mount the sequence controller 22 adjacent to the ceiling plate of the reagent reactor apparatus, however, the sequence controller may be mounted on the ceiling plate.

Figure 2:
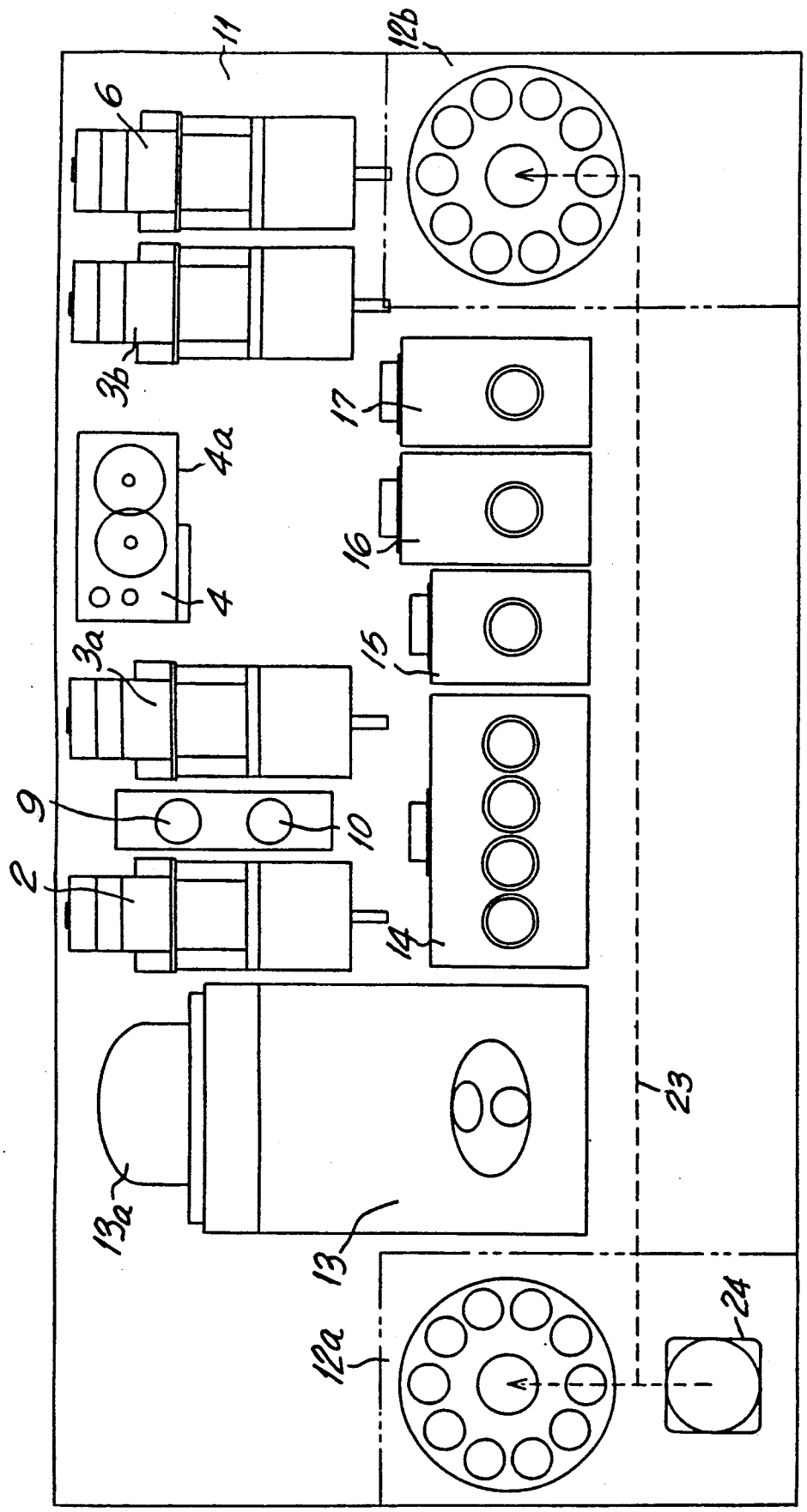
FIG. 2 is a plan view showing the principal sections of the reagent reactor apparatus shown in FIG. 1.

FIG. 2 is a plan view of the respective sections described with reference to FIG. 1. Parts corresponding to the parts shown in FIG. 1 are denoted by the same reference numerals as those of FIG. 1. That is, the following members are arranged on the front side of the base 11: the turn tables 12a and 12b, the centrifugal force applier 13, the temperature adjusting baths 14 through 17 arranged in the straight line as described previously. The following members are arranged on the back side of the base 11: a driving section 13a for driving the centrifugal force applier 13, the selecting valve 2 consisting of a disk valve, the measuring valves 3a and 3b, and the vacuum valve 6. Further, two electromagnetic valves 9 and 10 are disposed between the selecting valve 2 and the measuring valve 3a. The measuring device 4 is disposed between the measuring valves 3a and 3b. A driving section for driving the measuring device 4, which comprises a gear mechanism 4a, is mounted adjacent to the measuring device 4. The turn tables 12a and 12b intermittently rotate in synchronization with each other through a belt or chain transmission mechanism as shown by a broken line 23. A motor 24 for driving the turn tables 12a and 12b is mounted adjacent to the turn table 12a.

Next, the constructions of the respective sections are described below.

TURN TABLES ON START SIDE AND COLLECTING SIDE

Figure 3A:
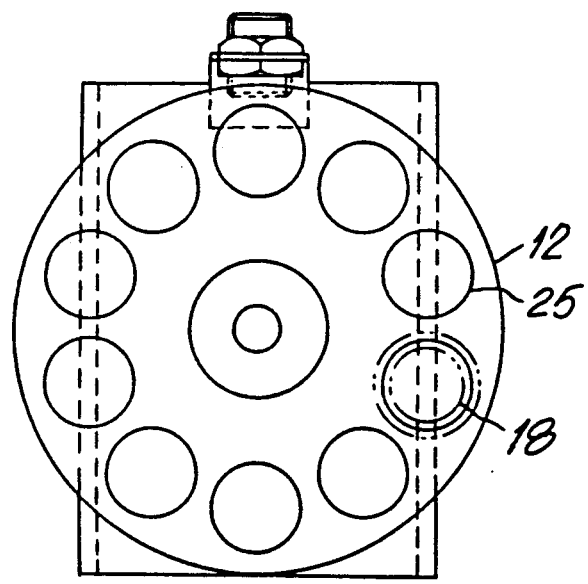
FIG. 3A is a plan view showing turn tables, disposed on the start and collecting sides, for transporting sample vials.
Figure 3B:
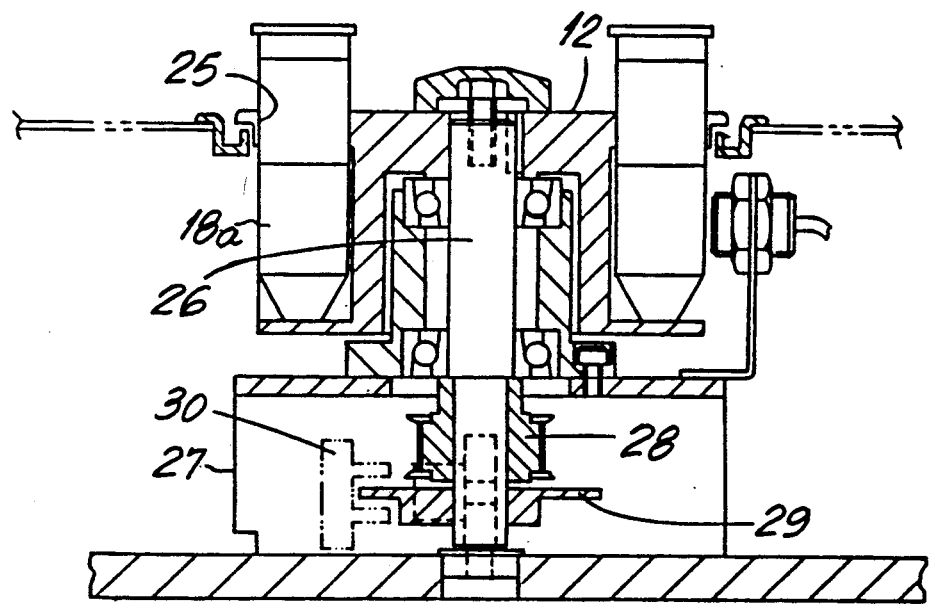
FIG. 3B is a sectional side elevational view of the turn tables, disposed on the start and collecting sides, for transporting sample vials.

FIGS. 3A is a plan view of the turn table 12a disposed on the start side and the turn table 12b disposed on the collecting side both having the same construction. FIG. 3B is a vertical sectional view thereof. The turn table 12 has ten vial supporting holes 25, each of which receives the vial 18 with the containing section 18a of the vial 18 disposed below the turn table 12. Belt pulley 28 are fixed to a supporting shaft 26 disposed in a driving section 27 located below the turn table 12. An index disk 29 having an appropriate positioning hole disposed directly below the belt pulley 28 is fixed to the supporting shaft 26. A photo-coupler 30 detects the positioning hole of the index disk 29 so that the turn tables 12a and 12b make an accurate intermittent rotation.

NOSE DRIVING SECTION

Figure 4:
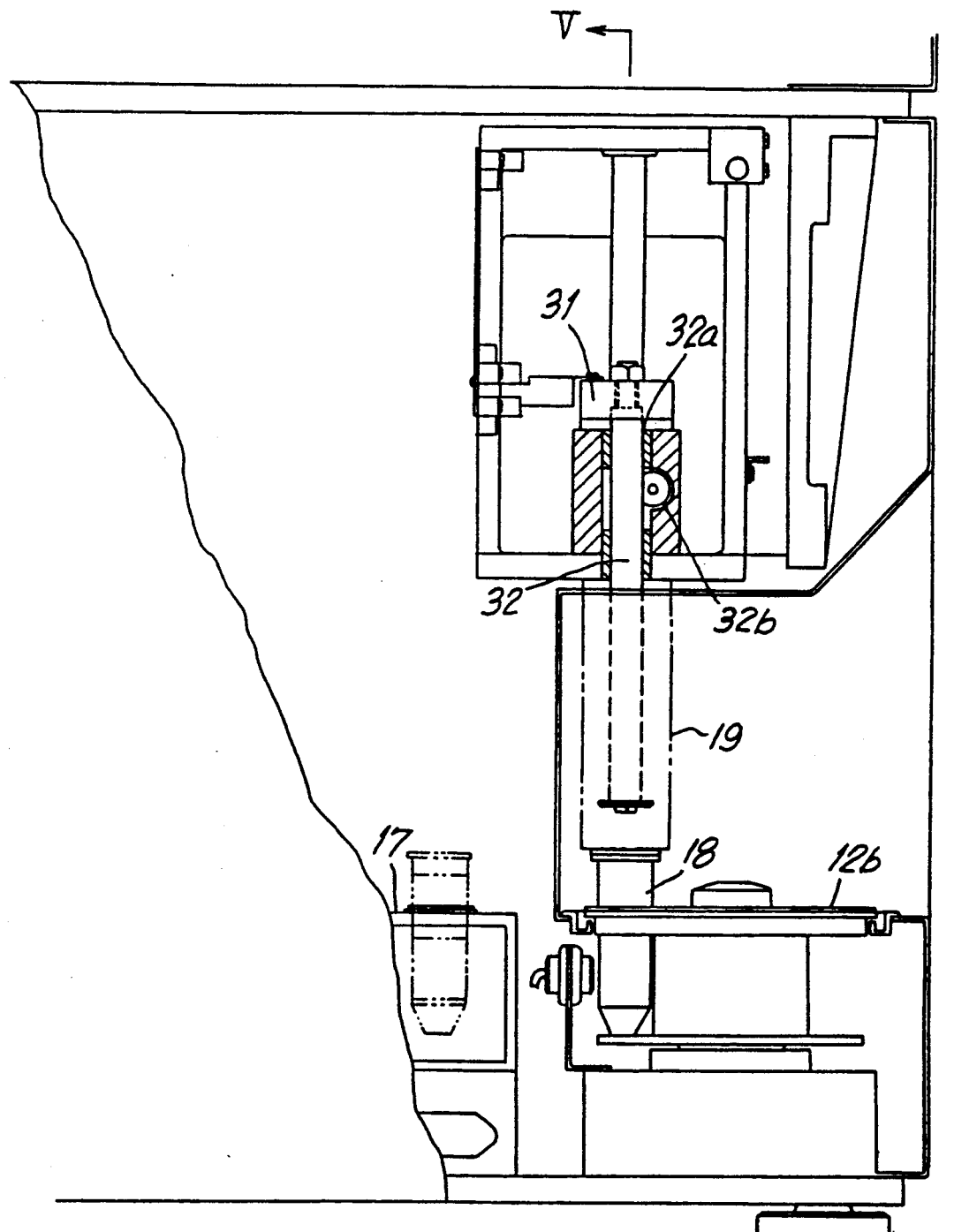
FIG. 4 is a partially cutaway sectional view showing the right side of the front of the reagent reactor apparatus.
Figure 5:
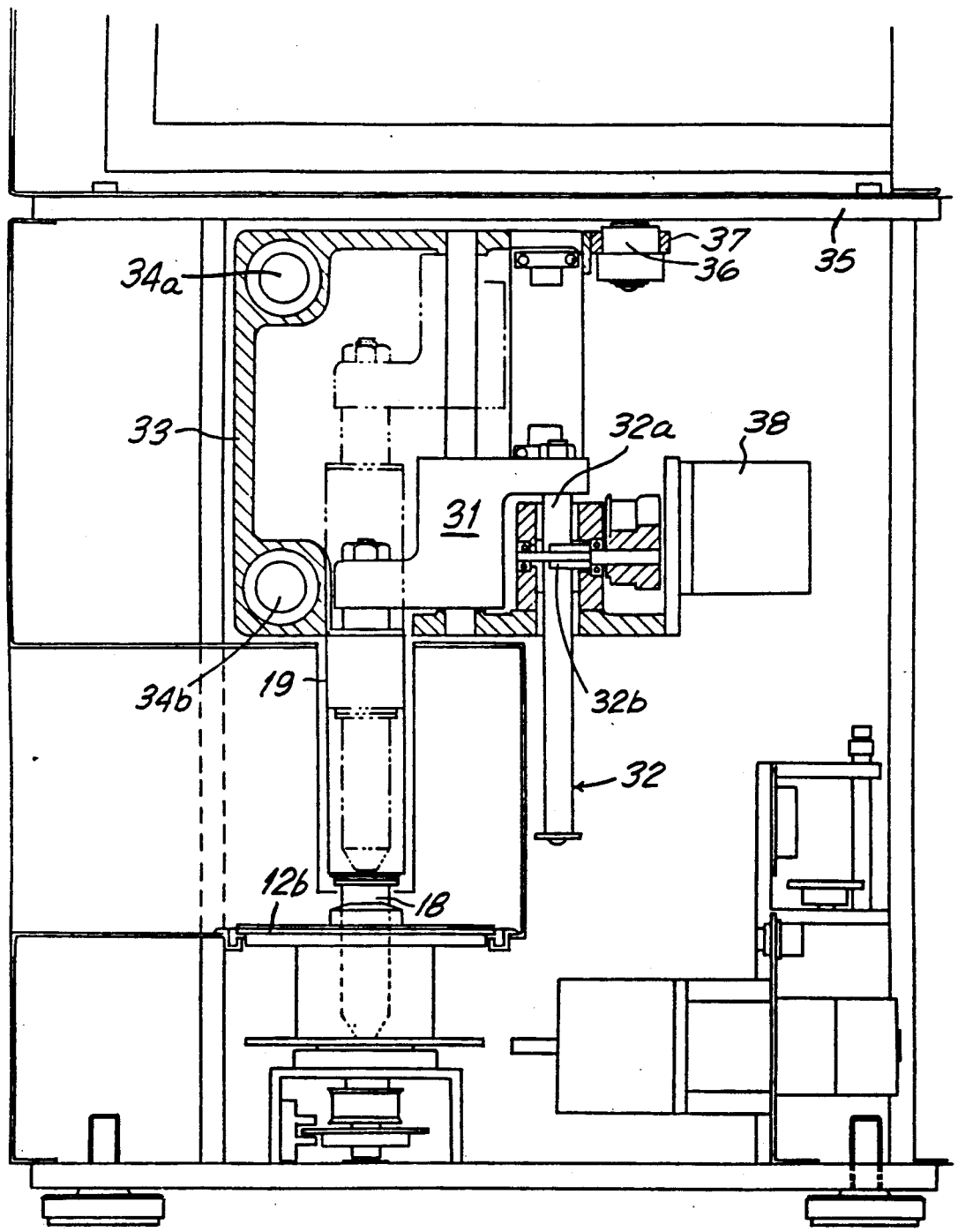
FIG. 5 is a sectional view taken along the lines V—V of FIG. 4.

FIGS. 4 and 5 show mechanisms for supporting and driving the nose section 19 which has engaged the vial 18 supported by the vial supporting hole of the turn table 12b. A rod 32 is supported to be downwardly projected by a nose block 31 which supports the top of the nose section 19. A rack 32a formed on the rod 32 is vertically driven by a pinion 32b. As shown by an imaginary line of FIG. 5, when the nose section 19 is located at the top position in the vertical movement thereof, the bottom end of the vial 18 is located above the tops of the vial receiving positions of the turn tables 12a, 12b, and the centrifugal force applier 13, and the temperature adjusting baths 14 through 17. Therefore, the vial 18 which has engaged the nose section 19 moves horizontally without colliding with any of the vial receiving positions. A movable block 33 which supports the nose driving mechanism is supported and guided to be horizontally movable by guide rails 34a and 34b parallel with the processing positions arranged in the straight line. The movable block 33 is horizontally moved by a belt 37 spanned between a pulley 36 supported by a ceiling plate 35. That is, the movable block 33 is connected with the belt 37. A motor 38 for driving the pinion 32b is disposed in the rear end of the movable block 33.

SAMPLE VIAL AND NOSE MEMBER

FIGS. 6A through 6C show conditions in which the vial 18 and the nose section 19 have engaged with each other. In these figures, regarding the nose section 19, only the bottom portion of the nose section 19 is sectionally shown. As described previously, the vial 18 comprises the containing section 18a and a valve sleeve 18b consisting of such as aluminum disposed above the containing section 18a. The top surface of the valve sleeve 18b is covered with a paramagnetic material 39. A plunger valve 40 is slidably accommodated in the vial 18. When the plunger valve 18 is located in the uppermost position thereof as shown in FIG. 6A, only the top portion of the plunger valve 40 penetrates into the containing section 18a, thus sealing the containing section 18a. When the plunger valve 40 has moved lowermost as shown in FIG. 6B, the fluid introducing port 41 of the vial 18 and a vacuum port 42 thereof serving as a fluid discharge port communicate with the containing section 18a. That is, since the opening of the fluid introducing port 41 and the opening of the vacuum port 42 are each disposed on the lower portion of the plunger valve 40, the respective openings are located in the containing section 18a at the top portion thereof when the plunger valve 40 has moved lowermost. The plunger valve 40 has at the top face thereof a concave at which each of the tops of the fluid introducing port 41 and the vacuum port 42 open to the outside. A shock absorbing rubber 43 having a conic projecting surface 43a is mounted on the concave. Two ports are formed through the shock absorbing rubber 43. One port which communicates with the fluid introducing port 41 opens at the apex of the conic projecting surface 43a. The other port which communicates with the vacuum port 42 opens at the conic surface. The nose section 19 comprises a nose main body 44 and a sleeve 45 disposed in the periphery of the nose main body 44. The lower end surface of the nose main body 44 is concaved. The concave matches the conic projecting surface 43a of the shock absorbing rubber 43 mounted on the plunger valve 40 of the vial 18. The sleeve 45 has at the lower end thereof a solenoid 46 which magnetically attracts the paramagnetic material 39 of the vial 18 in opposition thereto when the lower end of the nose main body 44 contacts the conic projecting surface 43a of the shock absorbing rubber 43 or the plunger valve 40 in such an extent as to press the plunger valve 40 downward slightly. The nose main body 44 has a fluid supply passage 47 and a vacuum sucking passage 48. The opening of the fluid supply passage 47 is formed in the center of the concave of the nose main body 44. The opening of vacuum sucking passage 48 is formed on the circular plane of the concave. The fluid supply passage 47 and the vacuum sucking passage 48 are connected to the measuring line 20 and the vacuum line 21 described previously referring to FIG. 1, respectively through the opening formed on the upper end surface of the nose main body 44. As apparent from FIGS. 6A and 6B, when the nose main body 44 contacts with the conic projecting surface 43a of the shock absorbing rubber 43, the opening formed on the lower end of the fluid supply passage 47 communicates with the upper end of the fluid introducing port 41 and the opening formed on the lower end of the vacuum sucking passage 48 communicates with the opening formed on the upper end of the vacuum port 42 of the plunger valve 40 through the circular space formed between the circular plane of the concave of the nose main body 44 and the conic projecting surface 43a of the shock absorbing rubber 43. Accordingly, the alignment of the axes of the nose section 19 and the vial 18 allows the passages of the nose section 19 and the vial 18 to be communicated with each other irrespective of the rotational angle of the vial 18. The main body of the plunger valve 40 consists of fluorine-contained polymer compact. The peripheral face of the upper end portion of the plunger valve 40 slidably vertically moves through the glass of the containing section 18a of the vial 18, thus allowing the containing section 18a to be airtight or gas to be released therefrom. FIG. 6C shows the state immediately before the sleeve 45 of the nose section 19 lifts the vial 18 by a magnetic force. As seen in FIG. 6C, the plunger valve 40 is located in the uppermost position thereof in the vial 18 and the lower end surface of the nose main body 44 and the top surface of the vial 18 are located in substantially the same plane with.

FIG. 6D shows the state in which the nose main body 44 is supported by the supporting section 44a thereof. Referring to FIG. 6B and 6D, it is understood that the nose main body 44 is supported by a pair of legs 50 provided in the supporting section 44a.

DISK VALVE

FIG. 7 shows the construction of a multiple disk valve to be used as the reagent selecting valve 2. As described previously, the measuring valves 3a, 3b, and the vacuum valve 6 shown in FIGS. 1 and 2 consist of a multiple disk valve (four-way valve), respectively. In FIG. 7, a nine-way valve used as the reagent selecting valve 2 is shown. The disk valve comprises a fluid introduction-discharge block 51 consisting of a comparatively thick disk, a passage block 52 adjacent thereto, and a rotary cone 53 adjacent thereto. According to the rotational angle of the rotary cone 53, any one of the circularly arranged nine introducing passages of the introduction-discharge block 51 and the discharge passage disposed in the center thereof communicate with each other through a communicating channel 53a. Referring to FIG. 7, reference numeral 51a denotes a fluid entrance, reference numeral 51b indicates a fluid outlet, and reference numeral 54 represents a supporting plate which supports the valve main body 55. Referring to FIG. 7A, an element 56 constituting part of the photocoupler is fixed to the supporting plate 54 at the left thereof and a positioning plate 58 which confronts the photo-coupler element 56 is supported by the rotary cone-supporting shaft 57 at the rear end thereof. Thus, the rotary cone 53 is rotated to carry out an appropriate passage connecting position.

WEIGHING INSTRUMENT

Figure 8A:
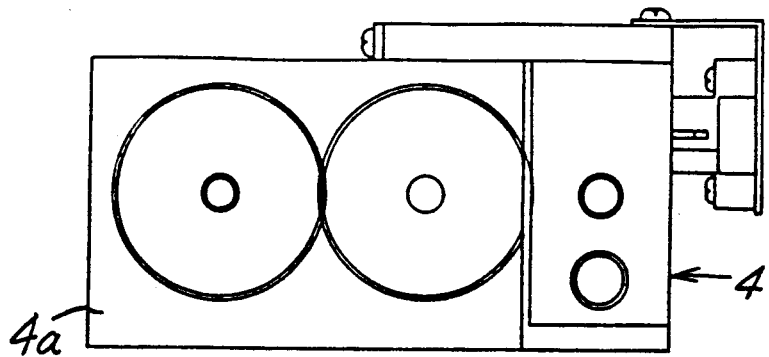
FIG. 8A is a plan view showing a measuring device and the mechanism for driving the measuring device.
Figure 8B:
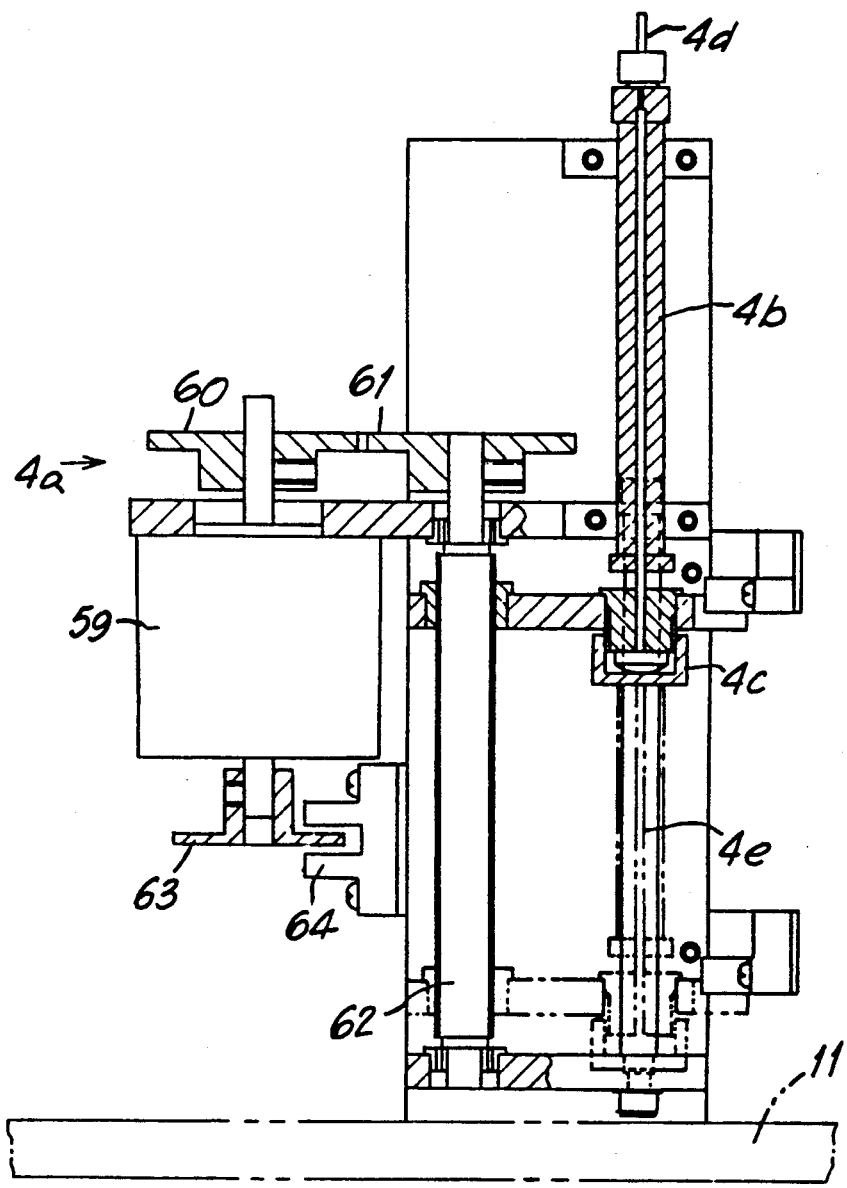
FIG. 8B is a vertical sectional view of the measuring device and the mechanism for driving the measuring device shown in FIG. 8A.

FIG. 8A and 8B show the detail of the measuring syringe section 4 of the measuring instrument and the measuring mechanism section 4a, respectively. Referring to FIG. 8B, the syringe chamber 4b of the syringe section 4 shown by a hatching shows the zero volume position. When the movable section 4c of the measuring syringe section 4 moves backward from this position to the position shown by an imaginary line, the maximum amount (for example, 100 μl) of a reagent can be introduced from a fluid introduction-discharge opening 4d disposed at the top of the syringe chamber 4b into the syringe chamber 4b. A plunger stroke adjusting bar 4e is disposed in the rear of the movable section 4c. The measuring mechanism section 4a comprises a motor 59, gears 60 and 61, a driving screw bar 62, a positioning disk 63 fixed to the motor shaft, and a photo-coupler 64.

CENTRIFUGAL FORCE APPLIER

Figure 9:
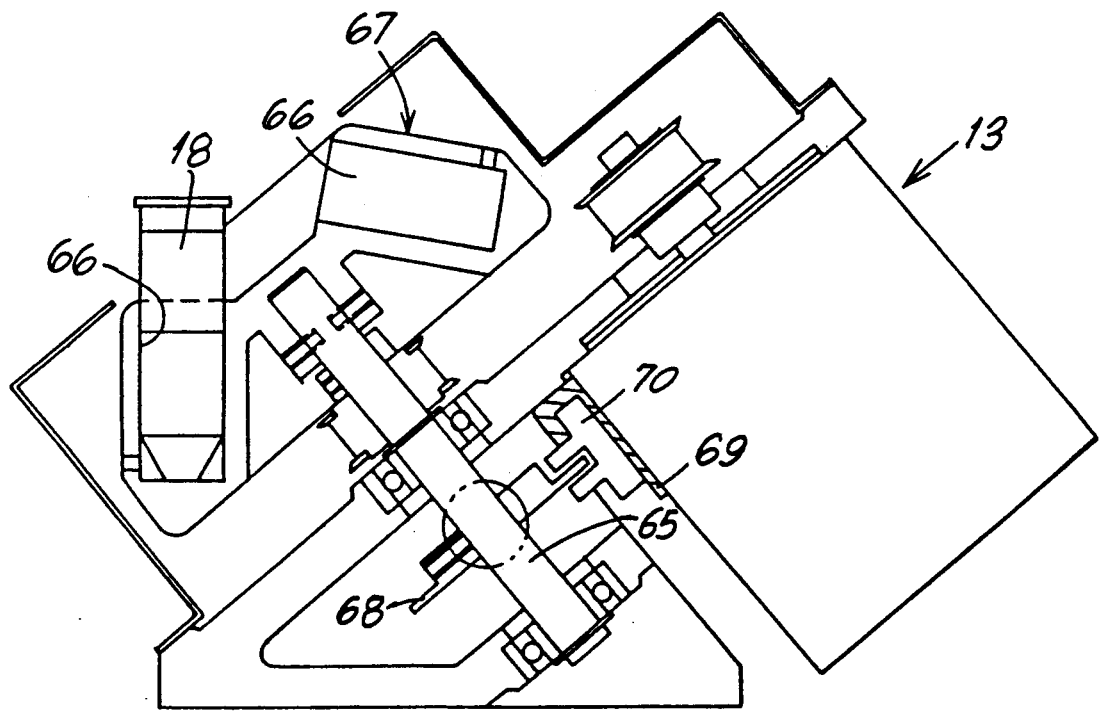
FIG. 9 is a vertical sectional view showing a centrifugal force applier.

FIG. 9 shows a vertical sectional view of a centrifugal force applier 13 serving as a liquid converging means. The left side thereof is drawn as the front of the reagent reactor apparatus. The axis 65 of a rotary cone inclines forward by a little more than 45° with respect to the base plate, or the horizontal line. The centrifugal force applier has an upper cover. The rotary cone 67 fixed to the axis 65 at the top thereof has at least two opening blocks each having a vial receiving hole 66 arranged circularly or being symmetrical with respect to the axis 65. The axes of the respective holes 66 make less than 45° with the axis 65. Thus, the vial receiving hole 66 which has reached the lowest point of the rotational orbit of the rotary cone is perpendicular to the base plate. At this time, the vial receiving hole 66 which has reached the highest point of the rotational orbit, namely, the point at which both vial receiving holes 66 are symmetrical with respect to the center of the rotational orbit is not parallel with the base plate, but makes a certain angle therewith, that is, the vial 18 inclines with the top thereof higher than the lower end thereof. A positioning disk 68 is mounted on the axis at a lower portion thereof and a photo-coupler 70 coupled with the positioning disk 68 is mounted on a holding block 69. Owing to this construction, the vial 18 is rotated after it is received by the vial receiving hole 66 disposed at the lowermost position of the rotational orbit of the rotary cone. Thus, a reagent located on the upper portion of the containing section 18a is converged to the lower end thereof by centrifugal force. If the centrifugal force applier 13 stops by some reason or other and the vial 18 remains held by the vial receiving hole 66 disposed at the highest point of the rotational orbit, the reagent contained in the vial 18 does not leak to the outside. This is because the opening of the vial 18 is held at a position much higher than the bottom thereof and the containing section 18a thereof is sealed by the plunger valve 40.

TEMPERATURE ADJUSTING BATH

Figure 10:
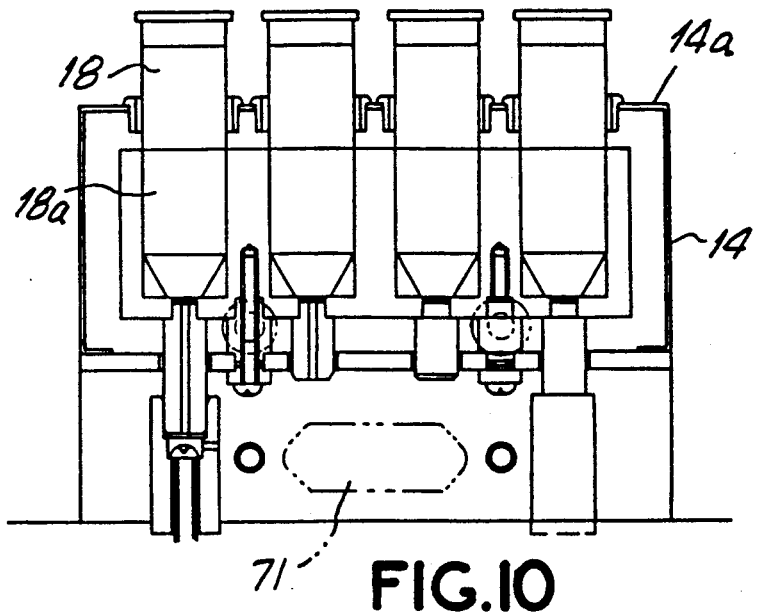
FIG. 10 is a sectional view of a temperature adjusting bath.

FIG. 10 shows a first temperature adjusting bath 14 which heats a reagent at 100°. The containing section 18a of the vial 18 is supported by the vial receiving hole of the temperature adjusting bath 14 at a position much lower than the position of the cover 14a thereof. The temperature adjusting bath 14 has an electric heating element. Referring to FIG. 10, a small frame 71 shown by an imaginary line denotes an electric terminal section connected to the heating element.

Although not shown in the drawings, the second, third, and fourth temperature baths 15, 16, and 17 for heating only one vial 18, respectively are formed similarly to the first temperature adjusting bath 14. Peltier element can be used to control the temperature of the third and fourth temperature adjusting baths 16 and 17 which heat a reagent at a comparatively low temperature, namely, 30° C. and 40° C., respectively so that the temperature adjusting baths 16 and 17 heat the reagent at 30° C. and 40° C., respectively or at a temperature lower than the room temperature.

The process for causing a reagent to react by the reagent reactor apparatus comprising the above construction is carried out as follows:

(1) Measuring

Figure 11A:
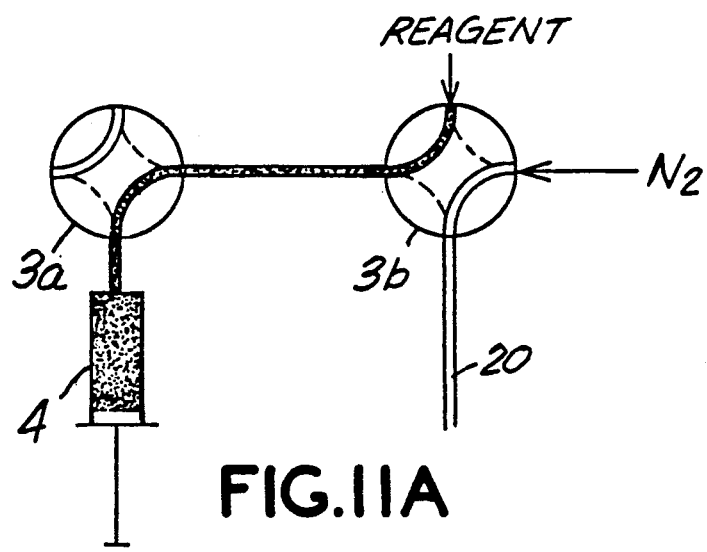
FIG. 11A through 11C are explanatory views showing the measuring of a reagent and a process for injecting the reagent into a sample vial.
Figure 11B:
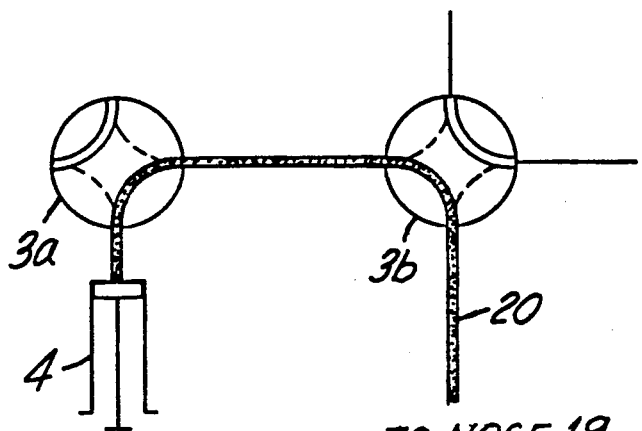

As shown in FIG. 11A, various kinds of agents are determined by a measuring instrument 4 (measuring syringe) driven by a pulse motor, then, the agents are introduced into the syringe and between the syringe and measuring valve 3b through the measuring valve 3a. Then, simultaneously with the switching of the measuring valve 3b from the condition as shown in FIG. 11A to the state as shown in FIG. 11B, a reagent contained in the syringe of the measuring instrument 4 is pushed out. Thereafter, a predetermined amount of the reagent is introduced into a measuring line 20 through the measuring valves 3a and 3b.

(2) Injection

Figure 11C:
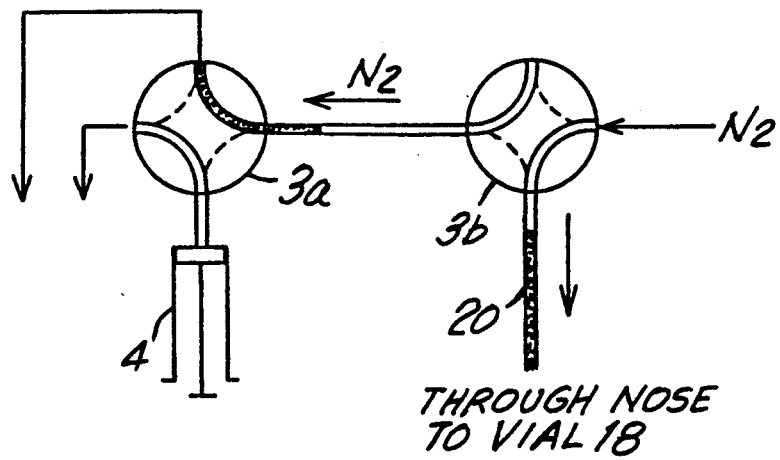

As shown in FIG. 11C, the measuring valve 3b is switched again and the nose section 19 is operated to introduce the reagent in the measuring line 20 into the vial 18 through the plunger valve 40 disposed therein.

(3) Centrifugal force application

The slide valve of the vial 18 is closed and the solenoid 46 of the nose section 19 is electrified so as to lift the vial 18. Thereafter, the vial 18 is rotated by the centrifugal force applier 13 (refer to FIG. 9) so that the reagent is dropped to the bottom of the vial 18.

(4) Substitution

The nose section 19 is operated to substitute a gas contained in the vial 18 with nitrogen gas through the plunger valve 40 (refer to FIG. 6B) disposed in the vial 18.

(5) Sealing

The nose section 19 is lifted to close the plunger valve 40 disposed in the vial 18.

(6) Heating

The plunger valve 40 disposed in the vial 18 is closed to electrify the solenoid 46 of the nose section 19. Thereafter, the vial 18 is lifted to transport the vial 18 to a predetermined reaction stage, namely, any one of the temperature adjusting baths 14 through 17.

(7) Cooling

The plunger valve 40 disposed in the vial 18 is closed to electrify the nose section 19. Thereafter, the vial 18 is lifted to transport the vial 18 to a reaction stage, namely, either the temperature adjusting baths 16 or 17.

(8) Unsealing

The nose section 19 is moved downward (refer to FIG. 6B) to open the plunger valve 40 disposed in the vial 18.

(9) Distillation removal

The nose section 19 is moved downward to open the plunger valve of the vial 18 so that the nitrogen gas is jetted into the vial 18 and at the same time, a vacuum pump is used to such the gas contained in the vial 18 so that the pressure inside the vial 18 is set to approximately 15 mmHg.

(10) Azeotropy

The nose section 19 is also moved downward to open the plunger valve of the vial 18 so that the nitrogen gas is jetted into the vial 18 and at the same time, a vacuum pump is used to suck the gas contained in the vial 18 so that the pressure inside the vial 18 is set to approximately 15 mmHg.

(11) Washing

The nose section 19 is moved downward and methanol is introduced into the vial 18 with the plunger valve disposed in the vial 18 closed. Thereafter, the nitrogen gas is jetted into the vial 18 to dry the vial 18.

The following is an embodiment of a process sequence of isolating a saccharide from a sample of a glycoconjugate and attaching a fluorescent label to the isolated saccharide to be performed before analyzing a labeled saccharide using the reagent reactor apparatus of the invention.

I. PROCESS SEQUENCE FOR DECOMPOSING HYDRAZINE

Decomposition of Hydrazine (1) Cooling 30° C.
(2) Measuring (anhydrous hydrazine/50 μl)
(3) Injection
(4) Washing
(5) Centrifugal force application
(6) Cooling 30° C.
(7) Substitution (Gas in vial is substituted with $N_2$)
(8) Heating 100° C., 10 hours
(9) Cooling 30° C.
(10) Measuring (toluene/20 μl)
(11) Injection
(12) Washing
(13) Centrifugal force application
(14) Cooling 30° C.
(15) Azeotropy 30° C., 20 minutes
(16) Measuring (toluene/20 μl)
(17) Injection
(18) Washing
(19) Centrifugal force application
(20) Cooling 30° C.
(21) Azeotropy 30° C.
(22) Measuring (toluene/20 μl)
(23) Injection
(24) Washing
(25) Centrifugal force application
(26) Cooling 30° C.
(27) Azeotropy 30° C.

N-acetylation

(28) Measuring (methanol solution containing 10% of pyridine/40 μl)
(29) Injection
(30) Washing
(31) Centrifugal force application
(32) Cooling 30° C.
(33) Measuring (acetic anhydride/10 μl)
(34) Injection
(35) Washing
(36) Centrifugal force application
(37) Cooling 30° C.
(38) Substitution
(39) Sealing 10 minutes
(40) Distillation removal 30° C., 20 minutes

Pyridyl Amination

(41) Measuring (Mixture solution of acetic acid containing 23M 2-aminopyridine and methanol at the ratio of 1:1/10 μl)
(42) Injection
(43) Washing
(44) Centrifugal force application
(45) Cooling 30° C.
(46) Substitution
(47) Heating 90° C., 15 minutes
(48) Distillation removal 90° C., 20 minutes
(49) Cooling 30° C.

Reduction

(50) Measuring (10 μl of methanol solution containing 10% of pyridylborane)
(51) Injection
(52) Washing
(53) Centrifugal force application
(54) Cooling 30° C.
(55) Substitution
(56) Heating 90° C., 30 minutes
(57) Cooling 30° C.
(58) Measuring (methanol/30 μl)
(59) Injection
(60) Centrifugal force application
(61) Heating 40° C.
(62) Azeotropy 40° C., 30 minutes
(63) Cooling
(64) Measuring (methanol/60 μl)
(65) Injection
(66) Centrifugal force application
(67) Heating 40° C.
(68) Azeotropy 40° C., 20 minutes
(69) Cooling 30° C.
(70) Measuring (water/100 μl)
(71) Injection
(72) Centrifugal force application

II. ACID HYDROLYSIS SEQUENCE (1) Cooling 30° C.
(2) Measuring (water solution of 4M trifluoroacetic acid/50 μl)
(3) Injection
(4) Washing
(5) Centrifugal force application
(6) Cooling 30° C.
(7) Substitution 100° C., 2 hours
(8) Heating 100° C., 2 hours
(9) Cooling 30° C.

The acid hydrolysis sequence to be carried out after step (10) is the same as that of hydrazine decomposition described above.

As described above, the reagent reactor apparatus in accordance with the invention is capable of carrying out a reagent reaction at a fast speed owing to the automated reaction process and the stabilized and high reaction yield owing to the reliable reaction process.

According to the embodiment, the vial is electromagnetically lifted by the nose section, however, it may be lifted by a permanent magnet or mechanically. The temperature adjusting baths are individually used according to each reaction stage, but it is possible to provide a program so that each of the temperature adjusting baths can be used for respective reaction stages. Further, nitrogen gas is used to introduce a reagent in the measuring line into the vial, however, other inert gases or the reagent itself may be used to push the reagent into the vial.

What is claimed is:

1. A reagent reaction apparatus comprising
a plurality of sample vials having on the top of the containing section thereof a plunger valve having a fluid introducing port and a fluid discharge port;

first vial indexing means for sequentially transporting said plurality of sample vials to a start position along a predetermined path;

second vial indexing means for receiving said sample vials at a collection position set a predetermined distance apart from said start position and sequentially feeding out said sample vials along a second predetermined path;

at least one temperature adjusting bath located between said start and collecting positions;

means, also located between said start and collecting positions, for converging liquid located in an upper portion of said sample vial to the bottom thereof by applying physical force from the opening of said sample vial toward the bottom thereof when said converging means has accepted said vial and vial operating means for transporting said sample vial from said start position to said collecting position, at which said sample vial is released from said vial operating means, by lifting said sample vial from start position to a predetermined transporting level, passing it to a position just above said collecting position, and lowering it from said transporting level to said collecting position; the passing of said sample vial to said position just above said collecting position by said operating means in the order according to a predetermined sequence program, including intermediate steps of forwardly or backwardly moving said sample vial to a position above either said at least one of the temperature adjusting bath or said converging means, lowering said sample vial thereinto where said sample vial operating means releases or grasps said sample vial to put it in or take out it from either said bath or said converging means, and lifting it up to the transporting level; and said vial operating means being provided with a fluid supply passage and a fluid discharge passage for selectively conveying any one of a plurality of reagents or an inert gas, wherein when said vial operating means holds one of said sample vials, the protruding ends of said passages respectively communicate with said fluid introducing port and said fluid discharge port formed in said plunger valve disposed in said sample vial; and said fluid introducing port and said fluid discharge port are opened by pressing said plunger valve downward with respect to the main body of said sample vial.

2. A reagent reactor apparatus as defined in claim 1 comprising:
a plurality of reagent sources;
a reagent selecting valve consisting of a valve having a plurality of entrances each connected to said reagent sources, an outlet, and said valve having a passage switching mechanism for selectively connecting any one of said entrances to said outlet;
a measuring instrument for measuring only the necessary amount of a reagent selected from said plurality of reagents;
an inert gas supply source; and
a measuring valve circuit for connecting said measuring instrument to either the outlet of said reagent selecting valve or the fluid supply passage of said vial operating means, wherein when said measuring instrument is connected to the outlet of said reagent selecting valve, said inert gas supply source is connected to the fluid supply passage of said vial operating means; and when said measuring instrument is connected to said fluid supply passage, a predetermined amount of a selected reagent is introduced into a conduit portion of the valve circuit communicated with said fluid supply passage.

3. A reagent reactor apparatus as defined in claim 1, wherein said first and second vial indexing means comprise turn tables having a plurality of vial receiving holes around the perimeter of the turn table and receiving a plurality of sample vials and intermittently rotating in synchronization with each other.

4. A reagent reactor apparatus comprising:
(A)
a sample vial including,
a containing section having an opening,
a valve sleeve fixedly connected to the opening of said containing section, part of which consists of a magnetic material,
a plunger valve fitting within said valve sleeve in cooperative relation therewith so as to penetrate into and withdraw from said containing section and having a fluid introducing port and a fluid discharge port each provided with an outside-connecting opening formed on the upper end face thereof and a containing section-communicating opening formed on the lower section thereof,
each of said containing section-communicating opening being exposed to said containing section when said plunger valve has penetrated into said containing section and the lower end section of said plunger valve engages the entrance of said containing section when said plunger valve has withdrawn, and
a retaining spring for retaining said plunger valve in the withdrawn position within said valve sleeve so as to seal said containing section by forcing said each containing section-communicating opening to be positioned outside said containing section, and within said valve sleeve and (B)
a movable nose assembly including,
a downward sleeve provided with a solenoid for selectively applying a magnetic attraction to a magnetic material mounted on said valve sleeve of said sample vial,
a nose main body held in said downward sleeve at a predetermined position thereof, the lower end of said nose main body contacting the upper end face of said plunger valve of said sample vial to such an extent as to press or said plunger valve downward slightly when said downward sleeve located directly above said sample vial is in a level from which said solenoid is capable of applying a magnetic force to said magnetic material, said nose main body being provided with a fluid supply passage and a fluid discharge passage each communicating with said respective outside-connecting openings of said fluid introducing port and said fluid discharge port formed in said plunger valve when said bottom thereof contacts said plunger valve or the conic projecting surface thereof, and
a movable holding member for holding said downward sleeve which holds said nose main body at said predetermined position thereof, said movable holding member allowing said downward sleeve and said nose main body to vertically move between the lowermost position in which said downward sleeve and said nose main body press downward said plunger valve of said sample vial to said position at which each of said containing section-communicating openings is exposed to said containing section when the lower end face of said nose main body contacts the top face of said plunger valve and the uppermost position in which said downward sleeve and said nose main body lift said sample vial by at least the whole length thereof with said solenoid magnetically attracting said magnetic material thereto, so that said movable nose is capable of accomplishing said lifting of said sample vial; and Wherein said fluid supply passage of said nose is selectively connected to a reagent supply source or an inert gas source and said fluid discharge passage of said nose is connected to a fluid sucking means so as to perform a process for sequentially injecting reagents into said sample vial and allowing reactions of said reagents according to a sequence program.

5. A reagent reactor apparatus as defined in claim 1, wherein said conveying means is centrifugal force applier comprising a rotary cone having at least a pair of holes for accommodating a plurality of sample vials, said holes being arranged thereon circularly or symmetrical with respect to the center of said rotary cone; the axis of each said holes making an angle less than 45° with the axis of said rotary cone and the axis of said rotary cone making an angle more than 45° with the horizontal base of the centrifugal force applier, so that the opening of said sample vial accommodated in said hole which is in the uppermost position of the rotational orbit of said rotary cone is in a position higher than the bottom thereof;

whereby centrifugal force is applied to liquid contained in said sample vial when said rotary cone is rotated after said sample vial has been deposited in said hole in the lowest position of the rotational orbit of the holes so that the liquid in said vial is forced to the bottom thereof, said rotary cone is interrupted in rotation for any one of said holes just in the lowermost position only of the rotational orbit to deposit one of the sample vials in and remove it from said any one of said holes.

* * * * *

UNITED STATES PATENT AND TRADEMARK OFFICE
CERTIFICATE OF CORRECTION

PATENT NO. : 5,089,230
DATED : February 18, 1992
INVENTOR(S) : Akihiro Kondo, Yoshiyuki Kato, Ikunoshin Kato, Hisao Tsuruta It is certified that error appears in the above-indentified patent and that said Letters Patent is hereby corrected as shown below:

Claim 4, Column 14, line 51, delete "or".

Signed and Sealed this

Fourteenth Day of December, 1993

Attest:

BRUCE LEHMAN

Attesting Officer     Commissioner of Patents and Trademarks